US008859207B2

(12) United States Patent  
Neckers et al.

(10) Patent No.: US 8,859,207 B2  
(45) Date of Patent: Oct. 14, 2014

(54) PHARMACEUTICAL COMPOSITIONS WHICH INHIBIT FKBP52-MEDIATED REGULATION OF ANDROGEN RECEPTOR FUNCTION AND METHODS OF USING SAME

(75) Inventors: Leonard M. Neckers, Bethesda, MD (US); Marc B. Cox, El Paso, TX (US); Jane B. Neckers, Bethesda, MD (US); Yeong Sang Kim, Gaithersburg, MD (US); Aki Iwai, Toride (JP); Yangmin Ning, Silver Spring, MD (US); Johanny Tonos de Leon, Frederick, MD (US); Heather Balsiger, El Paso, TX (US)

(73) Assignees: The United States of America, as represented by the Secretary, Department of Health and Human Services, Washington, DC (US); University of Texas at El Paso, El Paso, TX (US)

( * ) Notice: Subject to any disclaimer, the term of this patent is extended or adjusted under 35 U.S.C. 154(b) by 13 days.

(21) Appl. No.: 13/395,976

(22) PCT Filed: Sep. 14, 2010

(86) PCT No.: PCT/US2010/048705  
§ 371 (c)(1),  
(2), (4) Date: May 4, 2012

(87) PCT Pub. No.: WO2011/034834  
PCT Pub. Date: Mar. 24, 2011

(65) Prior Publication Data  
US 2012/0283215 A1 Nov. 8, 2012

Related U.S. Application Data

(60) Provisional application No. 61/242,541, filed on Sep. 15, 2009.

(51) Int. Cl.
| | |
|---|---|
| *C12N 15/00* | (2006.01) |
| *A61K 31/192* | (2006.01) |
| *A61K 31/167* | (2006.01) |
| *A61K 45/06* | (2006.01) |
| *A61K 31/4741* | (2006.01) |
| *A61K 31/165* | (2006.01) |
| *A61K 31/40* | (2006.01) |
| *A61K 31/4355* | (2006.01) |

(52) U.S. Cl.  
CPC ............. *A61K 31/192* (2013.01); *A61K 31/167* (2013.01); *A61K 45/06* (2013.01); *A61K 31/4741* (2013.01); *A61K 31/165* (2013.01); *A61K 31/40* (2013.01); *A61K 31/4355* (2013.01)  
USPC ...................... 435/6.13; 435/320.1; 514/44 R

(58) Field of Classification Search  
CPC ....................... A61K 31/4355; A61K 2300/00  
USPC .............................. 435/6.13, 320.1; 514/44 R  
See application file for complete search history.

(56) References Cited

U.S. PATENT DOCUMENTS

| 4,450,150 A | 5/1984 | Sidman |
| 6,686,357 B1 | 2/2004 | Wythes et al. |
| 7,205,437 B2 | 4/2007 | Dalton et al. |
| 2006/0084799 A1* | 4/2006 | Williams et al. ............. 536/23.5 |
| 2007/0099970 A1 | 5/2007 | Mackerell et al. |
| 2008/0293766 A1* | 11/2008 | Diamond et al. ............. 514/314 |
| 2010/0305082 A1* | 12/2010 | Downes et al. ............... 514/178 |

FOREIGN PATENT DOCUMENTS

WO WO 2004/032716 A2 4/2004

OTHER PUBLICATIONS

Brooks et al., "Response of rat ventral prostate to a new and novel 5α-reductase inhibitor," *Endocrinology*, 109 (3), 830-836 (1981).  
Brooks et al., "5α-reductase inhibitory and anti-androgenic activities of some 4-azasteroids in the rat," *Steroids*, 47 (1), 1-19 (1986).  
Buchwald et al., "Long-term, continuous intravenous heparin administration by an implantable infusion pump in ambulatory patients with recurrent venous thrombosis," *Surgery*, 88 (4), 507-516 (1980).  
Cheung-Flynn et al., "Physiological role for the cochaperone FKBP52 in androgen receptor signaling," *Mol. Endocrinol.*, 19 (6), 1654-1666 (2005).  
Cox et al., "The p23 co-chaperone facilitates dioxin receptor signaling in a yeast model system," *Toxicol Lett.*, 129 (1-2), 13-21 (2002).  
Estebanez-Perpina et al., "A surface on the androgen receptor that allosterically regulates coactivator binding," *Proc. Natl. Acad. Sci. U S A*, 104 (41), 16074-16079 (2007).  
Feau et al., "A high-throughput ligand competition binding assay for the androgen receptor and other nuclear receptors," *J. Biomol. Screen.*, 14 (1), 43-48 (2009).  
Goodson, "Dental Applications," *Medical Applications of Controlled Release*, 2, 115-138 (1984).  
Guo et al., "Abrogation of heat shock protein 70 induction as a strategy to increase antileukemia activity of heat shock protein 90 inhibitor 17-allylamino-demethoxy geldanamycin," *Cancer Res.*, 65 (22), 10536-10544 (2005).  
Hong et al., "Reciprocal binding of CTCF and Boris to the NY-ESO-1 promoter coincides with derepression of this cancer-testis gene in lung cancer cells," *Cancer Res.*, 65 (17), 7763-7774 (2005).  
International Search Report, Application No. PCT/US2010/048705, dated Mar. 22, 2011.

(Continued)

*Primary Examiner* — Brandon Fetterolf  
*Assistant Examiner* — Yih-Horng Shiao  
(74) *Attorney, Agent, or Firm* — Leydig, Voit & Mayer

(57) ABSTRACT

Pharmaceutical compositions that bind to a predicted FK506 Binding Protein 52 (FKBP52) interaction surface on the androgen receptor hormone binding domain, otherwise known as FKBP52 Targeting Agents (FTAs) are provided. These compositions of the present invention are found to specifically recognize the FKBP52 regulatory surface on the androgen receptor and inhibit FKBP52 from functionally interacting with the androgen receptor. Compositions comprising the pharmaceutical composition, as well as methods of use, treatment and screening are also provided.

1 Claim, 9 Drawing Sheets

(56) References Cited

OTHER PUBLICATIONS

Kadohama et al., "Retardation of prostate tumor progression in the Noble rat by 4-methyl-4-aza-steroidal inhibitors of 5α-reductase," *J. Natl. Cancer Inst.*, 74 (2), 475-486 (1985).

Kim et al., "Preparation of multilamellar vesicles of defined size-distribution by solvent-spherule evaporation," *Biochim. Biophys. Acta*, 812 (3), 793-801 (1985).

Langer, "New methods of drug delivery," *Science*, 249 (4976), 1527-1533 (1990).

Liang et al., "Binding of a 4-methyl-4-aza-steroid to 5α-reductase of rat liver and prostate microsomes," *Endocrinology*, 112 (4), 1460-1468 (1983).

Liang et al., "4-Azasteroidal 5α-reductase inhibitors without affinity for the androgen receptor," *J. Biol. Chem.*, 259 (2), 734-739 (1984).

Mayer et al., "Influence of vesicle size, lipid composition, and drug-to-lipid ratio on the biological activity of liposomal doxorubicin in mice," *Cancer Res.*, 49 (21), 5922-5930 (1989).

McConnell et al., "An inhibitor of 5α-reductase, MK-906, suppresses prostatic dihydrotestosterone in men with benign prostatic hyperplasia," *J. Urol.*, 141, 239A (1989).

Mumberg et al., "Yeast vectors for the controlled expression of heterologous proteins in different genetic backgrounds," *Gene*, 156, 119-122 (1995).

Petrow et al., "Inhibition of prostatic growth in rats by 6-methylene-4-3,20-dione," *J. Endocrinol.*, 95, 311-313 (1982).

Riggs et al., "The Hsp90-binding peptidylprolyl isomerase FKBP52 potentiates glucocorticoid signaling in vivo," *EMBO J.*, 22 (5), 1158-1167 (2003).

Riggs et al., "Noncatalytic role of the FKBP52 peptidyl-prolyl isomerase domain in the regulation of steroid hormone signaling," *Mol. Cell Biol.*, 27 (24), 8658-8669 (2007).

Saudek et al., "A preliminary trial of the programmable implantable medication system for insulin delivery," *N. Engl. J. Med.*, 321, 574-576 (1989).

Schreiber et al., "Rapid detection of octamer binding proteins with 'mini-extracts', prepared from a small number of cells," *Nucleic Acids Res.*, 17 (15), 6419 (1989).

Sefton, "Implantable pumps," *Crit. Rev. Biomed. Eng.*, 14 (3), 201-240 (1987).

Tranguch et al., "FKBP52 deficiency-conferred uterine progesterone resistance is genetic background and pregnancy stage specific," *J. Clin. Invest.*, 117 (7), 1824-1834 (2007).

Tranguch et al., "Cochaperone immunophilin FKBP52 is critical to uterine receptivity for embryo implantation," *Proc. Natl. Acad. Sci. USA*, 102 (40), 14326-14331 (2005).

Yano et al., "Inhibition of Hsp90 activates osteoclast c-Src signaling and promotes growth of prostate carcinoma cells in bone," *Proc. Natl. Acad. Sci. USA*, 105 (40), 15541-15546 (2008).

\* cited by examiner (Compound 1)

(Compound 2)

(Compound 3)

(Compound 4)

PHARMACEUTICAL COMPOSITIONS WHICH INHIBIT FKBP52-MEDIATED REGULATION OF ANDROGEN RECEPTOR FUNCTION AND METHODS OF USING SAME

CROSS-REFERENCE TO RELATED APPLICATIONS

This application is a U.S. National Phase of International Patent Application No. PCT/US10/48705, filed Sep. 14, 2010, which claims the benefit of U.S. Provisional Patent Application No. 61/242,541, filed Sep. 15, 2009, the entire contents of each of which are incorporated by reference in their entirety herein.

BACKGROUND OF THE INVENTION

Steroid hormone receptors including androgen receptor (AR), glucocorticoid receptor (GR), and the progesterone receptor (PR) require the ordered assembly of various chaperone and cochaperone proteins in order to reach a functional state. The final stage in the receptor maturation process requires the formation of a multimeric complex consisting of an Hsp90 dimer, p23, and one of several large immunophilins. Previously studies demonstrated that the large immunophilin, FK506-binding protein 52 (FKBP52), acts to potentiate GR, AR, and PR receptor signaling pathways, and FKBP52-mediated regulation of receptor function appears to be localized to the receptor hormone binding domain. In cellular studies, FKBP52 has been shown to preferentially regulate GR, AR, and PR receptor-mediated signal transduction. See, for example, Cheung-Flynn, J., et al., *Mol. Endocrinol.*, 19:1654-66 (2005); Riggs, D. L., et al., *EMBO J.*, 22:1158-67 (2003); and Tranguch, S., et al., *J. Clin. Invest.*, 117:1824-34 (2007). Given its receptor specificity, FKBP52 represents an attractive therapeutic target for the treatment of hormone-dependent diseases.

It has been shown that when certain molecules bind to a previously described surface region on the AR hormone binding domain called BF3, they can generally inhibit AR function in the 100 μM range. See, Estebanez-Perpina, E., et al., *Proc. Natl. Acad. Sci. USA*, 104:16074-9 (2007).

To date, the only known compounds for inhibition of AR function are related to selective AR modulators that bind to the hormone binding pocket, and are therefore competitive inhibitors of endogenous hormone binding. However, there still exists a need for compounds which are selective AR modulators which are not competitive agonists or antagonists to endogenous hormone binding.

BRIEF SUMMARY OF THE INVENTION

The present invention provides methods of use and treatment comprising the identified selective AR modulating compounds. In addition, the invention also provides assays to identify compounds which modulate AR function non-competitively, and represent a novel approach to inhibition of AR function. It is contemplated that these compounds, which inhibit FKBP52 enhanced AR function, are capable of being used in the treatment of AR, GR or PR related diseases.

In accordance with the present invention, the inventors have discovered a surface region on the AR hormone binding domain that, when mutated, displays a greater dependence on FKBP52 for normal function (FIG. 1).

As such, the present invention provides FKBP52 targeting agents (FTAs), which specifically inhibit FKBP52-enhanced steroid receptor activity. The FTAs of the present invention can specifically modulate steroid receptor function, including AR, GR, and PR function. Furthermore, the compounds of the present invention specifically inhibit FKBP52-enhanced AR function without binding the BF3 region of the AR, and are effective at concentrations that are less than those effective for AR function in the absence of FKBP52.

In an embodiment, the FTAs of the present invention include:

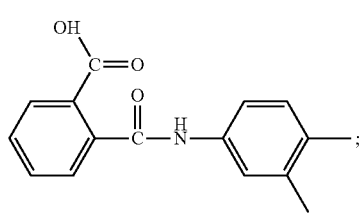
(Compound 1)

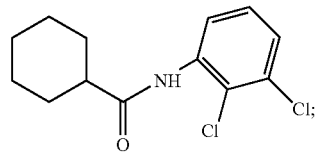
(Compound 2)

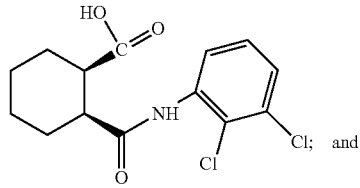
(Compound 3)

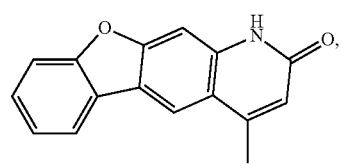
(Compound 4)

or pharmaceutically acceptable salts, solvates or stereoisomers thereof.

In an embodiment, the FTAs of the present invention are useful for treatment of a variety of hormone related medical conditions where androgenic, glucocorticoid and progesterone activity are upregulated when compared to normal levels, and where downregulation of androgenic, glucocorticoid or progesterone activity would provide a therapeutic effect. It is also understood that FTAs of the present invention are useful for treatment of a variety of hormone related medical conditions where androgenic, glucocorticoid and/or progesterone activity are downregulated when compared to normal levels, and where upregulation of androgenic, glucocorticoid and/or progesterone activity would provide a therapeutic effect.

In one embodiment, the present invention provides a method of treatment of prostate cancer in a mammal, comprising administering to the mammal, a composition comprising at least one FTA, wherein the composition includes a pharmaceutically and physiologically acceptable carrier, in an amount effective to inhibit prostate cancer cell growth.

It is also contemplated in an alternative embodiment, that the above method of treating prostate cancer includes administering one or more additional chemotherapeutic and/or anti-androgenic agents, such as bicalutamide (Casodex®), nilutamide (Nilandron®) flutamide, finasteride, and ketoconazole.

In another embodiment, the present invention provides a method of treatment of benign prostatic hyperplasia (BPH) in a mammal, comprising administering to the mammal, a composition comprising at least one FTA, wherein the composition includes a pharmaceutically and physiologically acceptable carrier, in an amount effective to inhibit BPH in the mammal.

In yet another embodiment, the method of treatment of BPH comprises administering one or more additional therapeutic agents, including anti-androgenic agents such as flutamide, and 5-alpha-reductase inhibitors such as finasteride, and ketoconazole.

In an embodiment, the present invention provides a method of treatment of non-insulin dependent diabetes (Type 2), or metabolic syndrome in a mammal, comprising administering to the mammal, a composition comprising at least one FTA, wherein the composition includes a pharmaceutically and physiologically acceptable carrier, in an amount effective to treat or diminish the symptoms of non-insulin dependent diabetes or metabolic syndrome in the mammal.

It is also contemplated that the method of treatment of non-insulin dependent diabetes (Type 2) or metabolic syndrome can include, in addition to at least one FTA, administering an additional therapeutic agent useful in the treatment of non-insulin dependent diabetes or metabolic syndrome in a mammal, such as one or more compounds from the class of compounds including sulfonylureas, metglitinides, biguanides, thiazolidinediones and DPP-4 inhibitors.

It is contemplated in an embodiment, that the present invention provides a method of inhibiting, or otherwise suppressing the fertility of a male mammal, comprising administering to the mammal, a composition comprising at least one FTA, wherein the composition includes a pharmaceutically and physiologically acceptable carrier, in an amount effective to inhibit spermatogenesis in the mammal.

It is also an embodiment of the present invention, to provide a method of inhibiting or otherwise suppressing the fertility of a female mammal, comprising administering to the mammal, a composition comprising at least one FTA, wherein the composition includes a pharmaceutically and physiologically acceptable carrier, in an amount effective to inhibit pregnancy in the mammal.

In addition to the methods of use of the FTAs provided above, the present invention also provides a mammalian model system and method for identification of novel FTAs. In an embodiment, the system comprises providing one or more AR test cells, the test cells comprising murine embryonic fibroblasts derived from FKBP-52 deficient mice (52KO MEFs), the cells being transfected with DNA encoding AR, an AR-responsive reporter plasmid, a constitutive lac Z reporter; and the FKBP52 protein, and providing one or more control cells, the control cells also comprising 52KO MEFs and being transfected with DNA encoding AR, an AR-responsive reporter plasmid, a constitutive lac Z reporter, and an empty vector, contacting the test and control cells with a test agent, followed by contacting the test and control cells with a AR agonist, incubating the cells for a period of time, and measuring the amount of AR-responsive reporter expression in the test and control cells to determine whether the test agent inhibited AR-responsive reporter expression in the test cells, when compared to the amount of AR-responsive reporter expression in the control cells.

BRIEF DESCRIPTION OF THE SEVERAL VIEWS OF THE DRAWING(S)

FIG. 1 is a depiction of the 3-dimensional structure of the AR hormone binding domain on which the predicted FKBP52 regulatory surface is delineated by a series of residues (1A), and the results of a yeast-based AR-mediated β-galactosidase reporter assay in the presence of wild-type or mutant AR, with or without a FKBP52 expression vector (1B) demonstrating increased FKBP52-dependence when the predicted FKBP52 regulatory surface is mutated.

Figure 5:
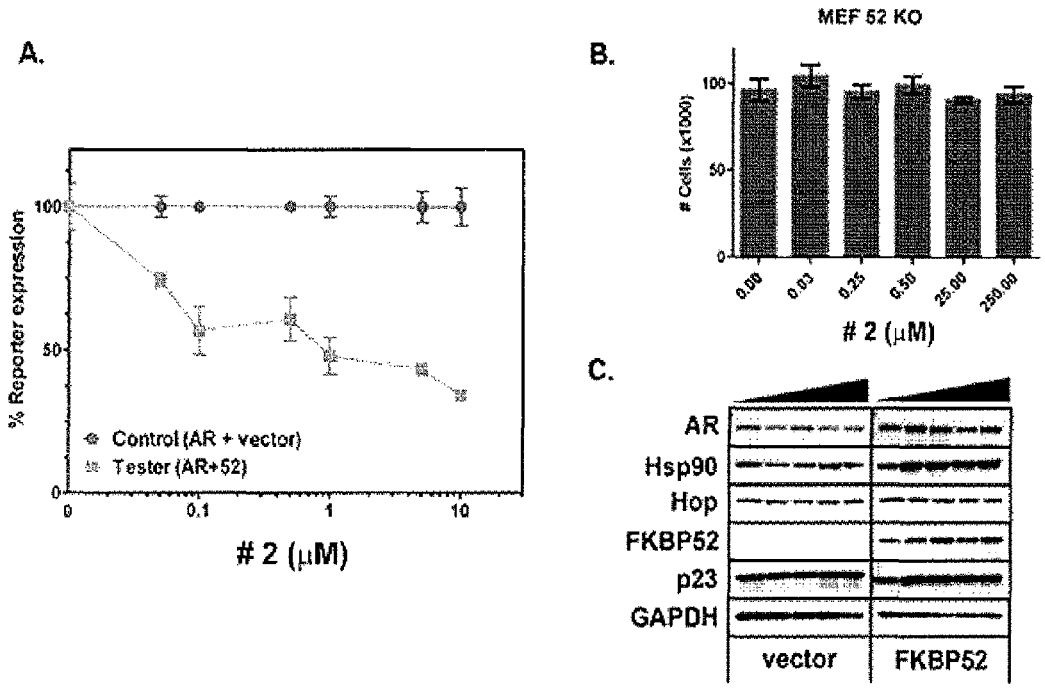

FIG. 5 shows inhibition of FKBP52-enhanced AR function with Compound 1 is consistent from yeast to mammalian cells. FIG. 5A shows data from an experiment using cells from a FKBP52 knock-out mouse embryonic fibroblast cell line (52KO MEF) transfected with AR, an AR-responsive reporter plasmid, a constitutive lac Z reporter plasmid, and which includes either an empty vector, or a vector with the FKBP52 gene, that were treated for 1 hour with the indicated concentrations of compound 2 followed treatment with hormone (di-hydroxy testosterone, DHT) for 16 hours prior to lysis and luciferase assay. FIG. 5B is a bar graph showing data from an experiment where 52KO MEF cells were treated at 50% confluency with a range of concentrations of Compound 2, and cell numbers were counted by trypan blue exclusion after 24 hours. FIG. 5C depicts Western blots on the same cell lysates from FIG. 5B, with compound 2 concentrations starting at 0, and increasing from about 0.1, 1, 10, to 100 μM.

Figure 6:
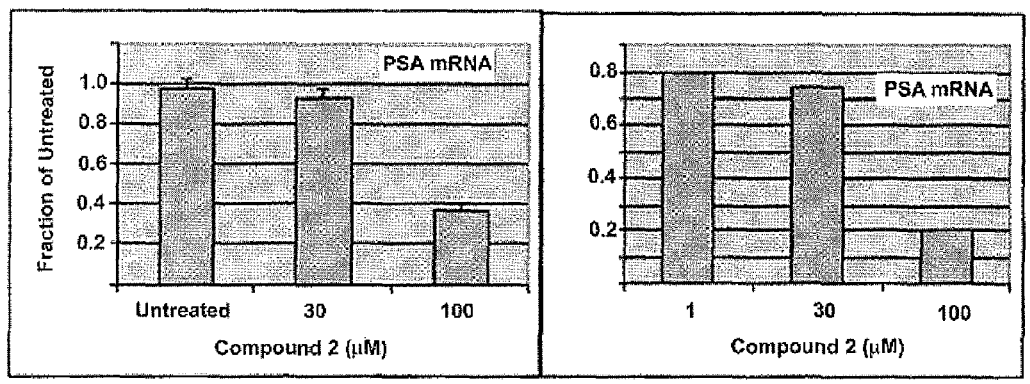

FIG. 6 illustrates RT-PCR analysis of Prostate Specific Antigen (PSA) mRNA and protein levels in the prostate cancer cell line LNCaP. Cells were treated with concentrations of Compound 2 ranging from about 0-100 μM, for 24 h (for mRNA), or for 48 h (protein). Data are expressed as a fraction of the value in untreated cells.

Figure 7:
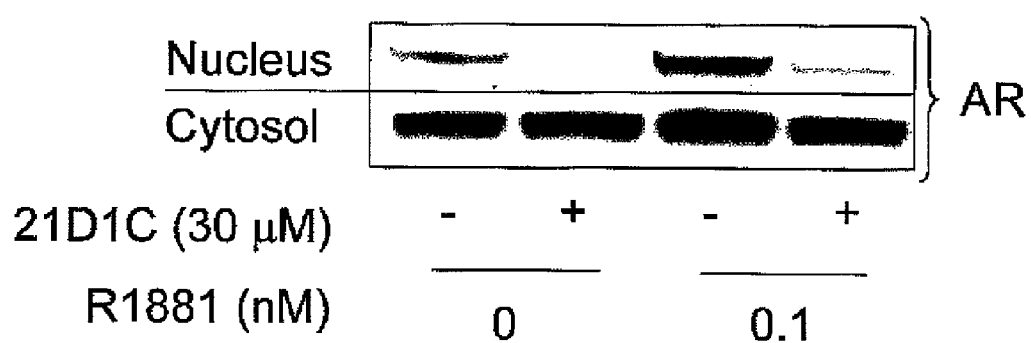

FIG. 7 illustrates measurement of AR nuclear translocation. Quantification of AR in nucleus and cytosol was performed by Western blotting with an AR-specific antibody following polyacrylamide gel electrophoresis. Appearance of AR in the nuclear fraction following R1881, represents ligand-dependent nuclear translocation of AR, which is significantly prevented by pre-treatment with the FTA (Compound 2).

Figure 8:
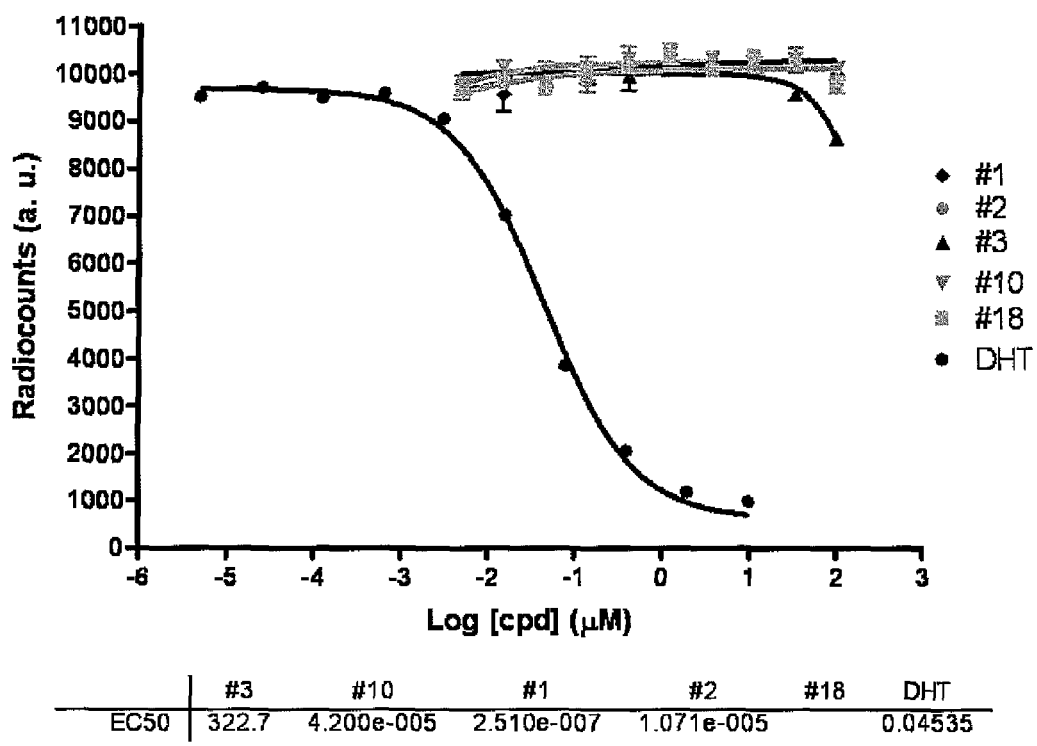

FIG. 8 is a graph of data from a scintillation proximity binding assay. The sigmoid curve shows the dose dependant binding of labeled DHT to the AR binding site. The flat curves to the right are the different concentrations of the claimed FTAs (compounds 1-3), as well as two other compounds tested (Compounds 10 and 18). The graph shows that none of the FTA compounds competitively inhibited DHT binding.

Figure 9A:
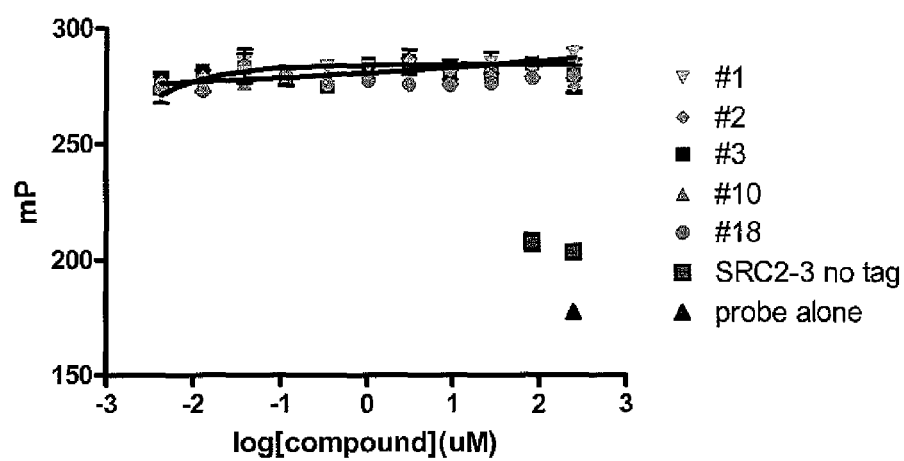
Figure 9B:
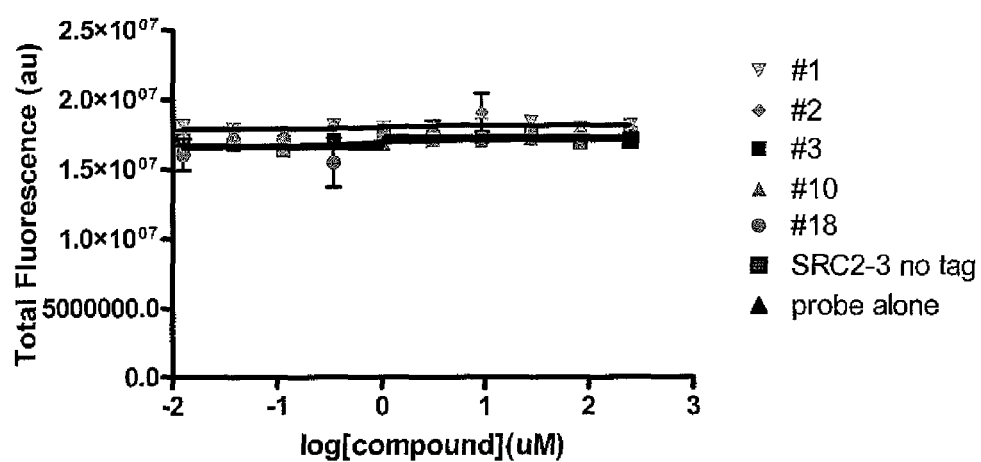

FIG. 9 provides two graphs of data from fluorescence polarization experiments. In FIG. 9A, fluorescently labeled SRC2-3 mimicking peptide was added as a probe to monitor interactions between FKBP52 and AR. The squared dark green dots are controls of two concentrations of unlabeled peptide showing a drop in the fluorescence polarization (mP) value when a displacement of the probe occurs. When SRC2-3 was tested the claimed FTAs (Compounds 1-3), as well as two other compounds tested (Compounds 10 and 18), did not show any competition for the FKBP52 binding site (curves are flat). In FIG. 9B, total fluorescence intensity is measured simultaneously as FP, to insure that no interference coming from the test compound itself is occurring in the assay. As we see, there is no change in total fluorescence detected for each FTA tested (same as in 9A), and there is no fluorescence interference, which confirms that mP values of FIG. 9A are valid. The legends for FIGS. 9A and 9B are the same as in FIG. 8.

DETAILED DESCRIPTION OF THE INVENTION

In an embodiment, the present invention provides FTAs which specifically inhibit FKBP52-enhanced steroid receptor activity. The FTAs of the present invention can specifically modulate steroid receptor function, including AR, GR, and PR function.

In an embodiment, the FTAs of the present invention include:

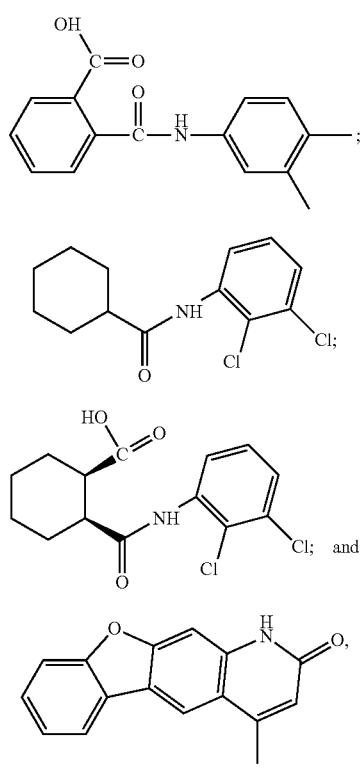

(Compound 1)

(Compound 2)

(Compound 3)

(Compound 4)

or pharmaceutically acceptable salts or solvates or stereoisomers thereof.

The FTAs of the present invention are useful for treatment of a variety of hormone related conditions where androgenic, glucocorticoid and/or progesterone activity are upregulated compared to normal levels, and downregulation of androgenic, glucocorticoid and/or progesterone activity would provide therapeutic effects. It is also understood that FTAs of the present invention are useful for treatment of a variety of hormone related medical conditions where androgenic, glucocorticoid and/or progesterone activity are downregulated when compared to normal levels, and where upregulation of androgenic, glucocorticoid and/or progesterone activity would provide a therapeutic effect.

In one embodiment, the present invention provides a method of treatment of prostate cancer in a mammal, comprising administering to the mammal, a composition comprising at least one FTA, wherein the composition includes a pharmaceutically and physiologically acceptable carrier, in an amount effective to inhibit prostate cancer cell growth.

It is also contemplated in an alternative embodiment, that the above method of treating prostate cancer includes administering one or more additional chemotherapeutic and/or anti-androgenic agents. For example, in an embodiment, treatment of prostate cancer in a mammal would comprise administering a composition comprising a FTA along with another anti-androgenic compound, such as bicalutamide (Casodex®), nilutamide (Nilandron®) flutamide, finasteride, and ketoconazole.

In another embodiment, the present invention provides a method of treatment of benign prostatic hyperplasia (BPH) in a mammal, comprising administering to the mammal, a composition comprising at least one FTA, wherein the composition includes a pharmaceutically and physiologically acceptable carrier, in an amount effective to inhibit BPH in the mammal.

In yet another embodiment, the method of treatment of BPH includes administering one or more additional therapeutic agents, such as 5-alpha-reductase inhibitors, such as finasteride or ketoconazole.

In another embodiment, the present invention provides a method of treatment of insulin independent diabetes or metabolic syndrome in a mammal, comprising administering to the mammal, a composition comprising at least one FTA, wherein the composition includes a pharmaceutically and physiologically acceptable carrier, in an amount effective to treat or diminish the symptoms of non-insulin dependent diabetes or metabolic syndrome in a mammal.

It is also contemplated that the method of treatment of non-insulin dependent diabetes or metabolic syndrome can include, in addition to a composition comprising at least one FTA, administering an additional therapeutic agent useful in the treatment of non-insulin dependent diabetes or metabolic syndrome in a mammal, such as one or more from the class of compounds including sulfonylureas, metglitinides, biguanides, thiazolidinediones and DPP-4 inhibitors. Examples of such compounds include metformin, glibenclamide, gliclazide, acarbose, rosiglitazone and pioglitazone.

It is contemplated in an embodiment, that the present invention provides a method of inhibiting or otherwise suppressing the fertility of a male mammal, comprising administering to the mammal, a composition comprising at least one FTA, wherein the composition includes a pharmaceutically and physiologically acceptable carrier, in an amount effective to inhibit spermatogenesis in a male mammal.

It is also an embodiment of the present invention to provide a method of inhibiting or otherwise suppressing the fertility of a female mammal, comprising administering to the mammal, a composition comprising at least one FTA, wherein the composition includes a pharmaceutically and physiologically acceptable carrier, in an amount effective to inhibit pregnancy in a female mammal.

It is also contemplated that the present invention can be used as a medicament for a range of disease conditions. Therefore, in an embodiment, the present invention provides a pharmaceutical composition selected from the group consisting of:

(Compound 1)

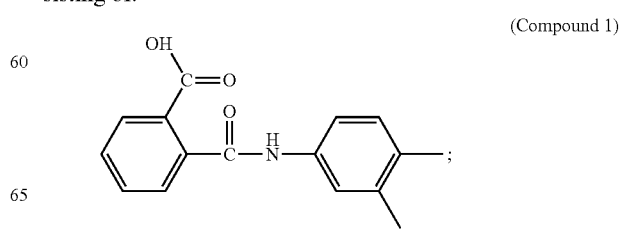

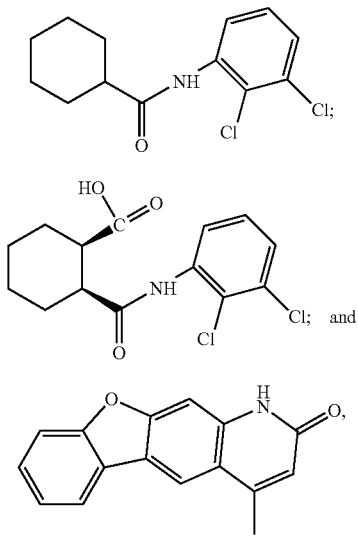

or pharmaceutically acceptable salts or solvates or stereoisomers thereof, wherein the composition includes a pharmaceutically and physiologically acceptable carrier, for use in an amount effective for use in a medicament, and most preferably for use as a medicament for treating one of a range of conditions, including, for example, prostate cancer, benign prostatic hyperplasia (BPH), insulin independent diabetes, or for use as a medicament for diminishment of the fertility of a male mammal, or for diminishment of the fertility of a female mammal.

With regard to the use of a medicament of the present invention for treatment of prostate cancer in a mammal, in an embodiment, the present invention would comprise administering a composition comprising a FTA along with another anti-androgenic compound, such as bicalutamide (Casodex®), nilutamide (Nilandron®) flutamide, finasteride, and ketoconazole.

Regarding the use of a medicament of the present invention for treatment of BPH in a mammal, in an embodiment, the present invention would comprise administering one or more additional therapeutic agents, such as 5-alpha-reductase inhibitors, such as finasteride or ketoconazole.

With regard to the use of a medicament of the present invention for treatment of insulin dependent diabetes in a mammal, in an embodiment, the present invention would comprise administering a composition comprising a FTA along with an additional therapeutic agent useful in the treatment of non-insulin dependent diabetes, or metabolic syndrome, in a mammal, such as one or more compounds from the class of compounds including sulfonylureas, metglitinides, biguanides, thiazolidinediones and DPP-4 inhibitors. Examples of such compounds include metformin, glibenclamide, gliclazide, acarbose, rosiglitazone and pioglitazone.

In addition to the methods of use of the FTAs provided above, the present invention also provides a mammalian model system and a method of using the model system to identify possible FTA compounds. In an embodiment, the method comprises providing one or more AR test cells, the test cells comprising 52KO MEF cells, the cells being transfected with DNA encoding AR, an AR-responsive reporter plasmid, a constitutive lac Z reporter, and the FKBP52 protein. The method also provides one or more control cells, wherein the control cells comprise 52KO MEF cells, and the cells are transfected with DNA encoding AR, an AR-responsive reporter plasmid, a constitutive lac Z reporter, and an empty vector. The test and control cells are contacted with a test compound, followed by contacting the test and control cells with a AR agonist, incubating the cells for a period of time, and measuring the amount of AR-responsive reporter expression in the test and control cells, in order to determine whether the test compound inhibited AR-responsive reporter expression in the test cells when compared to the amount of AR-responsive reporter expression in the control cells.

The inventors have surprisingly found that certain compounds heretofore having no known pharmacological activity are capable of inhibition of FKBP52-enhanced steroid receptor activity.

In an embodiment, the pharmaceutical composition of the present invention comprises the FTAs of the present invention together with a pharmaceutically acceptable carrier. Examples of the pharmaceutically acceptable carriers include soluble carriers such as known buffers which can be physiologically acceptable (e.g., phosphate buffer) as well as solid compositions such as solid-state carriers or latex beads.

It is also contemplated that the present invention further includes FTA derivatives. In one embodiment, the term "derivative" includes, but is not limited to, ether derivatives, acid derivatives, amide derivatives, ester derivatives and the like. Methods of preparing these derivatives are known to a person skilled in the art. For example, ether derivatives are prepared by the coupling of the corresponding alcohols. Amide and ester derivatives are prepared from the corresponding carboxylic acid by a reaction with amines and alcohols, respectively.

In addition, this invention further includes hydrates of the FTA compounds. The term "hydrate" includes but is not limited to hemihydrate, monohydrate, dihydrate, trihydrate and the like. Hydrates of the FTA compounds may be prepared by contacting the FTA with water under suitable conditions to produce the hydrate of choice.

In another embodiment, the invention provides a metabolite of the FTA compounds. In one embodiment, the term "metabolite" refers to any substance produced from another substance by metabolism or a through a metabolic process of a living cell or organ.

This invention further includes a process for preparing pharmaceutical products comprising the FTA compounds. The term "pharmaceutical product" means a composition suitable for pharmaceutical use (pharmaceutical composition), as defined herein. Pharmaceutical compositions formulated for particular applications comprising the FTAs of this invention are also part of this invention, and are to be considered an embodiment thereof.

The pharmaceutical compositions of the present invention are suitably used as therapeutic agents for cancer, including hormone related cancers, such as prostate cancer. According to another embodiment of the present invention, a method is provided for treating prostate cancer in a subject, comprising administering to the subject, a FTA of the present invention and/or its analog, derivative, isomer, metabolite, pharmaceutically acceptable salt, pharmaceutical product, hydrate, or N-oxide, or any combination thereof, in an amount effective to treat prostate cancer in the subject.

According to another embodiment of the present invention, a method is provided for delaying the progression of prostate cancer in a subject suffering from prostate cancer, comprising administering to the subject, a FTA of the present invention and/or its analog, derivative, isomer, metabolite, pharmaceutically acceptable salt, pharmaceutical product, hydrate, or N-oxide, or any combination thereof in an amount effective to delay or stop the progression of prostate cancer in the subject.

According to one embodiment of the present invention, a method is provided for administering the FTA compounds of the present invention to an FKBP52 modulated androgen receptor, by contacting the AR with a FTA compound and/or its analog, derivative, isomer, metabolite, pharmaceutically acceptable salt, pharmaceutical product, hydrate, or N-oxide, or any combination thereof, under conditions effective to cause the selective FTA to bind the FKBP52 modulated AR. The binding of the selective FTAs to the FKBP52 modulated AR can either enhance or inhibit the AR-hormone mediated cellular effect, depending on the FTA. For example, the addition of FTAs of the present invention inhibit the AR-hormone mediated effects and as such, the compounds of the present invention are useful as a male contraceptive and in a number of hormone therapies.

In another embodiment of the present invention, a method is provided for suppressing spermatogenesis in a subject, administering to the subject, a composition comprising a FTA of the present invention and/or its analog, derivative, isomer, metabolite, pharmaceutically acceptable salt, pharmaceutical product, hydrate, N-oxide, or any combination thereof, in an amount effective to bind the FTA to the FKBP52 protein modulating the androgen receptor and suppress spermatogenesis.

It is also an embodiment of the present invention, to provide a method of inhibiting or otherwise suppressing the fertility of a female mammal, comprising administering to the mammal, a composition comprising at least one FTA, wherein the composition includes a pharmaceutically and physiologically acceptable carrier, in an amount effective to inhibit pregnancy in the mammal.

Benign prostate hyperplasia (BPH) is a nonmalignant enlargement of the prostate gland, and is the most common non-malignant proliferative abnormality found in any internal organ, and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

In an embodiment, the present invention provides a method of treatment of BPH in a mammal comprising administering to the mammal, a composition comprising at least one FTA, wherein the composition includes a pharmaceutically and physiologically acceptable carrier, in an amount effective to inhibit BPH in the mammal.

In yet another embodiment, the above method of treatment of BPH includes administering to a subject, one or more additional therapeutic agents, such as 5-alpha-reductase inhibitors in combination with a FTA. In one embodiment, the 5-alpha-reductase inhibitor is MK-906, a product of Merck, Sharp & Dohme (McConnell et al., J. Urol. 141:239A (1989)). In another embodiment, the 5-alpha-reductase inhibitor is 17-β-N,N-diethylcarbamoyl-4-methyl-4-aza-5-α-androstan-3-one (4-MA) (Brooks et al., Endocrinology 109:830-836, (1981); Liang et al., Endocrinology 112:1460-1468 (1983)). In another embodiment, the 5-alpha-reductase inhibitor is a 4-azasteroid, which can be formed as in Liang et al., J. Biol. Chem. 259:734-739, (1984); and in Brooks et al., Steroids 47:1-19, (1986)). In another embodiment, the 5-alpha-reductase inhibitor is a 6-methylene-4-pregnene-3,20-dione, for example, as described (Petrow et al., J. Endocrinol. 95:311-313 (1982)). In yet another embodiment, the 5-alpha-reductase inhibitor is a 4-methyl-3-oxo-4-aza-5-α-pregnane-30(s) carboxylate (Kadohama et al., *J. Natl. Cancer Inst.* 74:475-486 (1985)).

In an embodiment, the FTAs of the present invention can also be combined with other testosterone decreasing compounds such as LH-RH agonists, for example. Drugs in this class include leuprolide (Lupron®, Viadur®) and goserelin (Zoladex®) for treatment of BPH and prostate cancer.

It has been recently shown that embryo implantation in the uterus is a critical step in mammalian reproduction, requiring preparation of the uterus in order to be receptive to blastocyst implantation. Uterine receptivity, also known as the window of implantation, lasts for a limited period of time, and it is during this period that blastocysts normally implant. The ovarian steroid hormones estrogen and progesterone ($P_4$) are the primary regulators of this process. The immunophilin FKBP52 serves as a cochaperone for steroid hormone nuclear receptors to govern appropriate hormone action in target tissues. See, Tranguch, S., et al., Proc. Nat. Acad. Sci. USA, 102(40):14326-14331 (2005). It was found that females missing the FKBP52 gene have complete implantation failure due to lack of attainment of uterine receptivity. The overlapping uterine expression of FKBP52 with nuclear progesterone receptor (PR) in wild-type mice together with reduced $P_4$ binding to PR, attenuated PR transcriptional activity and down-regulation of several $P_4$-regulated genes in uteri of $FKBP52^{-/-}$ mice, establishes this cochaperone as a potential regulator of uterine $P_4$ function.

As defined herein, in one or more embodiments, "contacting" means that the FTA of the present invention is introduced into a sample containing the AR, and/or FKBP52 and appropriate enzymes or reagents, in a test tube, flask, tissue culture, chip, array, plate, microplate, capillary, or the like, and incubated at a temperature and time sufficient to permit binding of the FTA to the FKBP52 protein or the FKBP52-AR complex. Methods for contacting the samples with the FTA, or other specific binding components are known to those skilled in the art, and may be selected depending on the type of assay protocol to be run. Incubation methods are also standard and are known to those skilled in the art.

In another embodiment, the term "contacting" means that the FTA compounds of the present invention are introduced into a subject receiving treatment, and the FTAs are allowed to come in contact with the FKBP52-AR complex in vivo.

As used herein, the term "treating" includes preventative as well as disorder remitative treatment. The terms "reducing", "suppressing" and "inhibiting" have their commonly understood meaning of lessening or decreasing. In addition, as used herein, the term "progression" means increasing in scope or severity, advancing, growing or becoming worse. Also, the term "recurrence" means the return of a disease after a remission.

In the present invention, in one embodiment, a suitable pharmaceutical composition is one in which the FTA of the present invention is anchored on a liposome and which can also contain a toxin, an anti-cancer drug or the like. The liposome used for anchoring the FTA may be composed of a lipid bilayer. Alternatively, the liposome used may be composed of a multiple lipid layers or composed of a single lipid layer. Examples of the constituents of the liposome include phosphatidyl choline, cholesterol and phosphatidyl ethanolamine, and further include phosphatidic acid as a substance for imparting the liposome with electric charge. The ratio of those constituents is, for example, 0.3 to 1 mole, preferably 0.4 to 0.6 mole of cholesterol, 0.01 to 0.2 mole, preferably 0.02 to 0.1 mole of phosphatidyl ethanolamine, and about 0 to 0.4 mole, preferably about 0 to 0.15 mole of phosphatidic acid per 1 mole of phosphatidylcholine.

The methods of producing the liposome may be by any known conventional methods. For instance, they can be produced using a method in which a mixture of the lipids, from which a solvent has been removed, is emulsified by a homogenizer or the like, and then subjected to freeze-thawing to obtain a multilamellar liposome, followed by adjustment of pore size of the liposome appropriately by ultrasonication, high-speed homogenization, or pressure filtration through a membrane having uniform-size pores (Biochimica et *Biophysica Acta.,* 812:793-801 (1985)). In an embodiment, it is contemplated that the liposomes have a particle size of about 30 to about 200 nm.

In an embodiment, examples of the pharmaceutical agents to be encapsulated in the liposome in addition to the FTAs include: carcinostatic agents such as adriamycin, daunomycin, mitomycin, cisplatin, vincristine, epirubicin, methotrexate, 5-Fu (5-fluorouracil) and aclacinomycin; toxins such as ricin A and diphtheria toxin; and antisense RNA. Encapsulation of the FTA into the liposome may be accomplished by hydration of the lipids with an aqueous solution of the agent. In addition, adriamycin, daunomycin and epirubicin may be encapsulated into the liposome by a remote-loading method using a pH gradient (*Cancer Res.,* 49:5922-30 (1989)).

It is also contemplated that carcinostatic or anticancer agents can be combined with the FTAs of the present invention without the use of liposome carriers as well.

In one embodiment, the carrier is a pharmaceutically acceptable carrier. With respect to pharmaceutical compositions, the carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g. corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include sodium chloride solution, Ringer's dextrose, dextrose and sodium chloride, lactated Ringer's and fixed oils. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the FTA compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular FTA, as well as by the particular method used to administer the FTA. Accordingly, there are a variety of suitable formulations of the pharmaceutical composition of the invention. The following formulations for parenteral, subcutaneous, intravenous, intramuscular, intraarterial, intrathecal, and interperitoneal administration are exemplary and are in no way limiting. More than one route can be used to administer the FTA, and in certain instances, a particular route can provide a more immediate and more effective response than another route.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the FTAs in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

For purposes of the invention, the amount or dose of the FTA administered should be sufficient to effect, e.g., a therapeutic or prophylactic response, in the subject over a reasonable time frame. The dose will be determined by the efficacy of the particular FTA and the condition of a human, as well as the body weight of a human to be treated.

The dose of the FTA also will be determined by the existence, nature and extent of any adverse side effects that might accompany the administration of a particular FTA. Typically, an attending physician will decide the dosage of the FTA with which to treat each individual patient, taking into consideration a variety of factors, such as age, body weight, general health, diet, sex, FTA to be administered, route of administration, and the severity of the condition being treated. By way of example, and not intending to limit the invention, the dose of the FTA can be about 0.001 to about 1000 mg/kg body weight of the subject being treated/day, from about 0.01 to about 10 mg/kg body weight/day, about 0.01 mg to about 1 mg/kg body weight/day.

Alternatively, the FTA can be modified into a depot form, such that the manner in which the FTA is released into the body to which it is administered is controlled with respect to time and location within the body (see, for example, U.S. Pat. No. 4,450,150). Depot forms of FTA can be, for example, an implantable composition comprising the FTA and a porous or non-porous material, such as a polymer, wherein the FTA is encapsulated by or diffused throughout the material and/or degradation of the non-porous material. The depot is then implanted into the desired location within the body and the FTAs are released from the implant at a predetermined rate.

In one embodiment, the pharmaceutical compositions provided herein are controlled release compositions, i.e., compositions in which the FTA is released over a period of time after administration. Controlled or sustained release compositions include formulation in lipophilic depots (e.g., fatty acids, waxes, oils). In another embodiment the composition is an immediate release composition, i.e., a composition in which all of the FTA is released immediately after administration.

In yet another embodiment, the pharmaceutical composition can be delivered in a controlled release system. For example, the agent may be administered using intravenous infusion, an implantable osmotic pump, a transdermal patch, or other modes of administration. In an embodiment, a pump may be used (see Langer, Science 249:1527-1533 (1990); Sefton, CRC Crit. Rev. Biomed. Eng. 14:201-401 (1987); Buchwald et al., Surgery 88:507-516 (1980); Saudek et al., N. Engl. J. Med. 321:574-576 (1989). In one embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, vol. 2, pp. 115-138 (1984)). Other controlled release systems are discussed in the review by Langer, supra.

The compositions of the present invention may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts). Such compositions will influence the physical state, solubility, stability, rate of in vivo release, and rate of in vivo clearance.

Also contemplated in the present invention are FTAs modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the FTA's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain the FTA as an active component is well understood in the art, for example by mixing, granulating, or tablet-forming processes. In an embodiment, the FTA ingredient is mixed with excipients which are pharmaceutically acceptable and compatible with the active ingredient. For oral administration, the FTAs or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the FTAs or their physiologically tolerated derivatives, such as salts, esters, N-oxides, and the like are converted into a solution, suspension or emulsion, if desired, with the substances customary and suitable for this purpose, for example, solubilizers.

Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the FTAs will be pharmaceutically acceptable salts. Other salts may, however, be useful in the preparation of the compounds according to the invention or of their pharmaceutically acceptable salts. Suitable pharmaceutically acceptable salts of the compounds of the present invention include acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

EXAMPLES

Example 1

Yeast AR-Mediated Reporter Assay

To investigate FTA inhibitory activity, a modified yeast-based assay was created to screen an in-house compound library. The receptor-mediated β-galactosidase assays were initially based on published methods ((Riggs D L, et al., EMBO J., 22:1158-67 (2003); Cox M B, et al., Toxicol. Lett. 129:13-21 (2002) and Balsiger, H. A., and Cox, M. B., in Methods in Molecular Biology: The Nuclear Receptor Superfamily, vol. 505. Edited by I. J. McEwan. The Humana Press, Totowa, N.J. (2008)), however, the assay methods were modified substantially to allow use of a 96-well plate format. All cDNAs for the FKBP proteins were obtained from the laboratory of David Smith at the Mayo Clinic, Arizona. The AR-P723S mutant was originally described previously (Cheung-Flynn, J. et al. (2005)).

All receptors and FKBP proteins were expressed from a set of yeast expression vectors that are commercially available (Mumberg, D., et al., Gene 156: 119-122 (1995)). Four yeast strains were prepared as shown in the table below.

TABLE 1

| Name | (Strain number) | receptor | Immunophilin |
|---|---|---|---|
| AR-723 + V | (DSY1479) | AR-P723S | Empty vector |
| AR-723 + 51 | (DSY1481) | AR-P723S | FKBP51 |
| AR-723 + 52 | (DSY1483) | AR-P723S | FKBP52 |
| AR + V | (DSY1496) | AR (wild-type) | Empty vector |

The DSY numbers in the table above are internal reference numbers for cataloguing purposes. The assay is designed to study the effect of the test compounds on AR activiation. The DHT concentration used for the β-galactosidase assays in liquid culture were optimized in order to maximize the difference between cells carrying an empty vector (control strain) versus cells carrying an FKBP52 expression vector (tester strain) and typically range from about 1 to 10 nM, depending upon the strain of yeast and plasmids used.

The standard hormone signaling "tube assay" requires that 5 ml cultures be cultivated in 50 ml conical tubes and monitored for growth and β-galactosidase activity during the 2 hour time course of induction. The use of an AR mutant that is hyper-responsive to FKBP52 makes this end point using a 96-well plate method feasible.

FKBP52 strongly potentiates GR and AR signaling (about 5- to 10-fold). In these yeast strains, the immunophilins are expressed from the strong, constitutive GDP promoter on a 2 micron plasmid (about 20 copies per cell), using a plasmid-encoded HIS3 gene as a selectable marker to maintain the plasmid. A yeast vector containing a 2 micron origin of replication is considered by those of skill in the art to be a high copy number plasmid that can be present at up to 20 plasmid copies per cell, as opposed to the low copy number CEN plasmids that replicate at up to 4 copies per cell. The use of a GPD promoter and 2 micron origin of replication maximizes expression levels in the assay. In the yeast system using the tube assay, it was found that the AR-P723S receptor requires much higher levels of DHT than the wild-type receptor to function. However, FKBP52 rescues the function of AR-P723S to the level of the wild-type receptor (data not shown). The net result is that strains containing FKBP52 have up to 50-fold higher levels of AR transactivation at limiting concentrations of DHT compared to strains lacking FKBP52. These receptors are expressed from the GPD promoter on a 2 micron, TRP1-marked plasmid.

All of the strains contain the β-gal reporter gene controlled by a weak, HRE-dependent CYC1 promoter. This is also a 2 micron plasmid, but it carrys the URA3 gene. This reporter can be activated by both GR and AR. Thus this reporter was used in all of the SAR assays described herein.

The yeast host strain used to make these four strains, W303, has his3, trp1 and ura3 mutations, so that growth on media lacking tryptophan, histidine and uracil requires the presence of all three plasmids. The URA3-marked steroid receptor-mediated β-galactosidase reporter plasmid (pUCΔss-26X) was the gift of Dr. Brian Freeman, University of Illinois. The pleiotropic drug resistance 5 (PDR5) gene was deleted in this strain, because PDR5 is an ATP-binding cassette transporter that could potentially transport the test compounds out of the cells, thereby hindering their identification. By deleting PDR5, this potential problem is avoided. The tester strain contains a LEU2-marked human AR-P723S expression plasmid, and a TRP1-marked human FKBP52 expression plasmid. The AR-P723S mutant has a proline replaced by a serine at amino acid 723, and is hypersensitive to FKBP52 potentiation thereby enhancing the sensitivity of the assay. The control strain contains a LEU2-marked wild type human AR expression plasmid alone. The use of this strain controls for specificity and general toxicity, including effects on growth, transcription, translation and protein stability.

The strains were cultivated overnight using a shaking incubator in SC-HUW medium (synthetic complete medium lacking histidine, uracil and tryptophan). The next morning the cultures were diluted back to an optical density (OD) of 0.05 units with warm medium. One hundred microliters of culture medium was added to the wells containing 10 μl of hormone. The 96 well plates were incubated at 30° C. for two hours, then 100 μl of chemiluminescent Gal-screen assay reagent (Applied Biosystems-Tropix) was added to each well. This reagent contains the β-gal substrate in a lysis buffer suitable for yeast. About one hour later, the plate was read in a luminometer. The measured RLU (relative light units) was normalized to the cell density of the cultures, at the time they were added to the plates, to give a measure of RLU/OD unit. This procedure corrects for minor differences in cell density between the strains. For simplicity, the RLU/ODU was divided by 1000 so that the signaling values range up to 10 units.

The FTA compounds tested were dissolved in dimethyl sulfoxide (DMSO) as the vehicle, and Applicants have found that the yeast in this assay can tolerate up to 5% DMSO without significant effects on the assay results. Thus, care is taken not to exceed the 5% DMSO limit. The protocol was modified to test for drug sensitivity by adding aliquots of culture to wells containing the serially diluted drug (in growth medium), and after 30 min incubation at 30° C. the hormone was added.

From the previous experiments, it was determined that 50 nM DHT would provide both a strong signal and significant FKBP52 potentiation (data not shown). The SAR assays were performed in a similar manner as the library screening assays except the FTA compounds to be tested were purchased and tested at a range of concentrations. In addition, the compounds were tested for effects on wild type AR and also GR. Because the inventors were only interested in compounds that display FKBP52-specific inhibition, the data were normalized for each receptor to the vector alone control strain, and the normalized data for each compound were plotted on the same graph with all three receptors.

The inventors began testing compounds in the assay by starting with a standard concentration of about 50 μM for all compounds tested. After any "hits", a second round of assays were performed which involved a titration of test compound to establish the $IC_{50}$. An AR specific hormone (10 nM DHT) is added 30 minutes after compound addition, but it can be added any time from about 30 minutes to 2 hours later. At about 2-4 hours later, preferably about 2.5 hours later, about 100 μl of Tropix Gal-Screen® reagent (Applied Biosystems, Foster City, Calif.) is added to each well. The plates are incubated for approximately another 1-3 hours, preferable about 1 hour and 30 minutes, and the light emission is measured on a microplate luminometer (Luminoskan Ascent, Thermo Labsystems). Thus, in these examples, 96 compounds can be screened on two plates (tester and control) in only 4 hours. Those compounds which inhibited FKBP52-enhanced receptor function but did not affect AR function alone were further analyzed.

Figure 1:
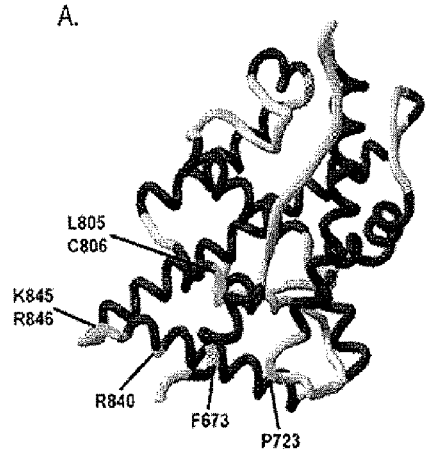
Figure 1:
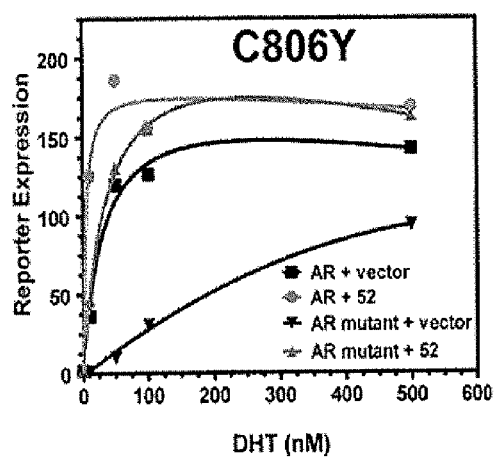
Figure 2:
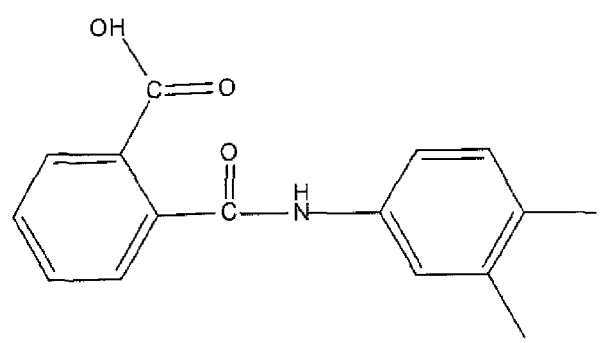
FIG. 2 is an illustration showing the compound designated Compound 1.

The result of the initial high-throughput screen was the identification of a compound (Compound 1) which inhibits FKBP52-enhanced AR function, but does not affect AR function alone in yeast (FIG. 2).

Example 2

Characterization of the FKBP52 Inhibition in a Mammalian Model System

To further characterize the compounds of interest selected from the yeast library assay, the inventors created a mammalian model system, comprising a receptor-mediated luciferase reporter assay, using in a murine embryonic fibroblast cell line (MEF) which has the gene for FKBP52 knocked out (52KO MEFs). The system was created to assess the effects of the inhibitors on FKBP52 regulation of receptor function (Tranguch S., et al., Proc. Natl. Acad. Sci. USA, 102:14326-14331 (2005)). To control for specificity and general toxicity, the inventors assessed the effects of the inhibitors on receptor function in the absence of FKBP52. Dose response curves were prepared to determine the half maximal inhibitory concentration ($IC_{50}$) for the compounds tested. The half maximal lethal dose ($LD_{50}$) was also determined for all cell types used in these studies. The $LD_{50}$ was determined by performing dose response curves in which the measure of toxicity will be cell death (via trypan blue exclusion).

The 52KO MEF cells provide a true FKBP52 negative background in which to test the FKBP-specific effects of FTAs and they are amenable to transfection. Additionally, FKBP51 protein levels in the 52KO MEF cells are nearly undetectable. Thus, the AR mutants identified above are subcloned into a mammalian expression vector and transfected into the 52KO MEFs, along with the various immunophilins, and assayed for hormone-induced expression of a luciferase reporter gene.

The 52KO MEF cells used to characterize inhibitor effects in mammalian cells were obtained from Dr. David Smith at the Mayo Clinic, and have been previously characterized. See Cheung-Flynn, J, et al., Mol. Endocrinol., 19(6):1654-66 (2005).

Example 3

Luciferase Assays and Western Immunoblots in 52KO MEFs

Figure 3:
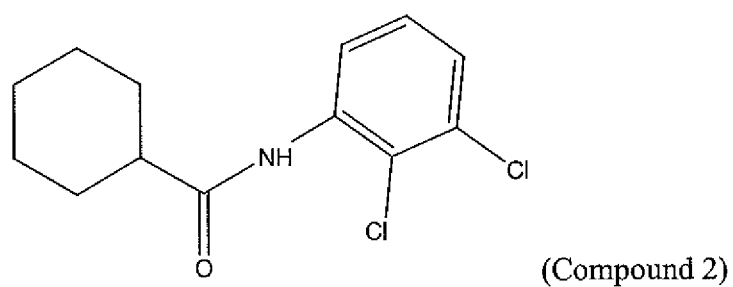
FIG. 3 depicts the structures of three additional compounds which were found to be positive for inhibition of FKBP52-enhanced AR function.
Figure 3:
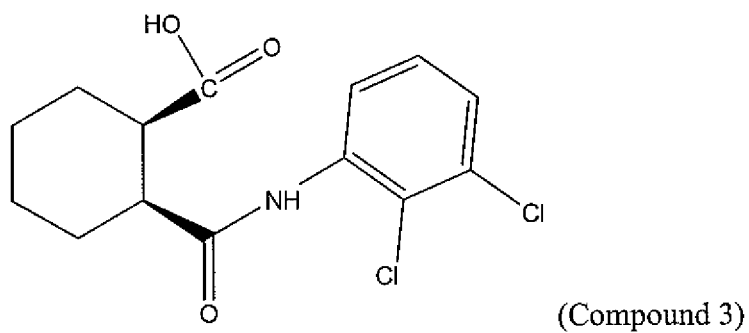
Figure 3:
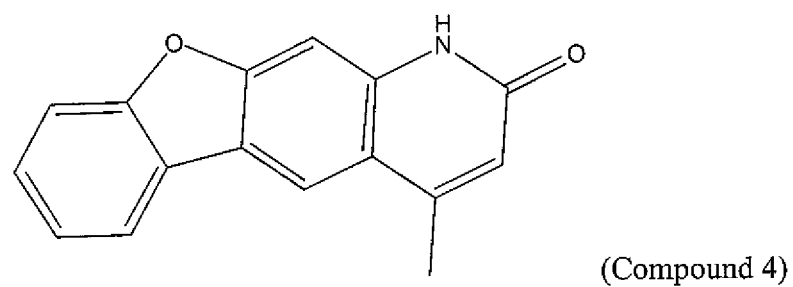
Figure 4:
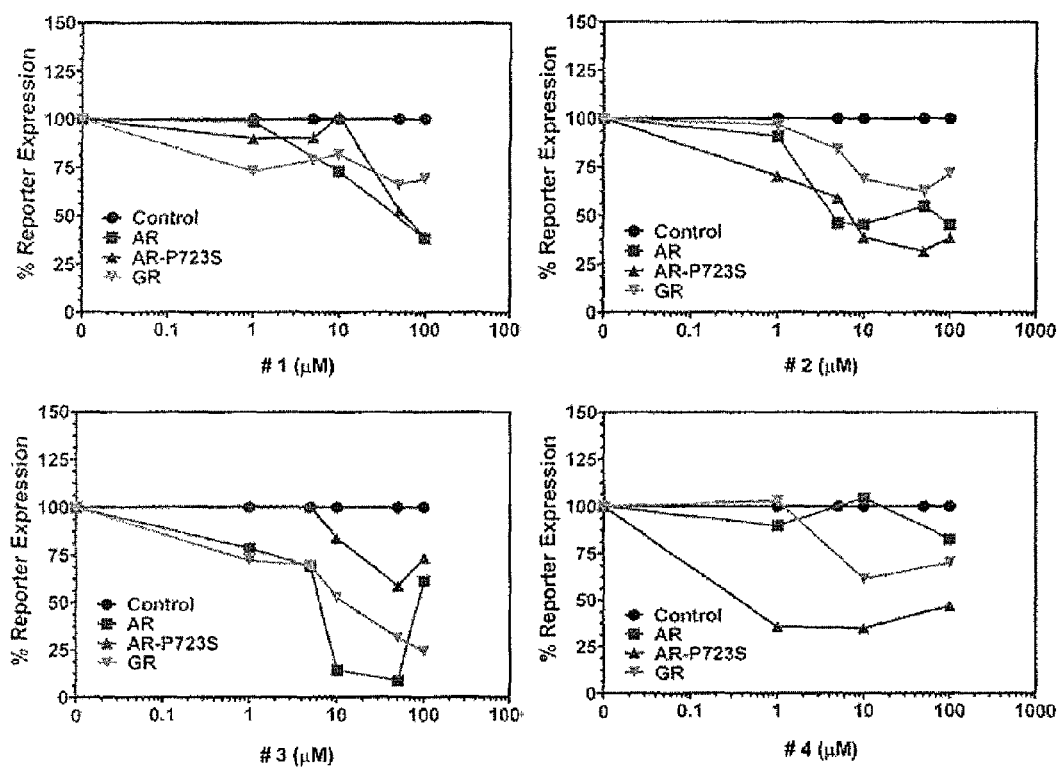
FIG. 4 depicts inhibition curves for the four compounds that were selected in the initial SAR analysis, and later tested in vitro.

In order to identify further compounds with AR inhibitory activity and AR selectivity, a structure-activity analysis was performed on Compound 1, which resulted in the identification of additional compounds that represented structural modifications. These compounds were then assayed to test structure-activity relationships (SAR), and as a result, three other compounds were identified and selected for further study as shown in FIG. 3.

All of the compounds tested in the initial SAR analysis are commercially available, and were purchased from Sigma-Aldrich (3050 Spruce St. St. Louis, Mo. 63103), with the exception of Compound 4, which was provided by Dr. Leonard Neckers. Compounds 2 and 3 are not included in the regular Sigma-Aldrich catalogue, but can be purchased through Sigma's rare chemicals library.

In an embodiment, 52KO MEFs were cultured at 5% $CO_2$ in MEM medium, supplemented with 10% FBS and essential amino acids. Plasmid transfections were performed in 6-well plates at approximately 80% confluence for about three hours, using Lipofectamine 2000 (Invitrogen, Carlsbad, Calif.), at a DNA (μg):Lipofectamine (μl) ratio of 1:3, in MEM without FBS. To control for expression and protein stability, the cells are lysed around 48 hours after transfection in M-PER (Pierce, Rockford, Ill.) and Western immunoblots were then performed using standard procedures, and were immunostained for glyceraldehyde 3-phosphate dehydrogenase (GAPDH) (6C5; Biodesign International, Saco, Minn.) as a loading control.

For the FKBP52 AR activity assays, 52KO MEFs are transfected with the following plasmids (1 μg each plasmid/well): a hormone-responsive firefly luciferase reporter, a mammalian expression vector (pCI-neo; Promega, Madison, Wis.) constitutively expressing AR or AR mutants, and a pCI-neo plasmid constitutively expressing the FKBP52 protein. To control for transfection efficiency, each well was transfected with about 50 ng of a constitutive β-galactosidase expression plasmid. At about twenty-four hours post-transfection, cells were treated with a AR specific hormone (DHT) in an ethanol carrier (concentration of ethanol in media should not exceed about 0.01%). The cells were then lysed 10-20 hours later, preferably about 16 hours after hormone addition, by addition of M-PER (Pierce, Rockford, Ill.; 200 μl/well) and incubated at room temperature for 15 minutes. Luciferase activity was determined by addition of 100 μl luciferase assay reagent (Promega, Madison, Wis.) to 10 μl cell lysate in an opaque 96-well plate; light emission was then measured immediately in a microplate luminometer (Luminoskan Ascent, Thermo Labsystems).

β-galactosidase activity was measured by addition of 100 μl Tropix Gal-Screen assay reagent (Applied Biosystems, Foster City, Calif.) to about 6 μl lysate in an opaque 96-well plate. After about 2 hours at room temperature, plates were assayed using a microplate luminometer. After normalizing for transfection efficiency (relative light units/β-galactosidase activity), the data was plotted as fold induction of luciferase activity over background activity observed in the absence of hormone.

Example 4

Receptor-FKBP52 Co-Immunoprecipitations

In an embodiment, radiolabeled wild type receptors (AR, PR and GR) and receptor mutants will be generated by in vitro transcription/translation (TnT Kit, Promega, Madison, Wis.) in the presence of [$^{35}$S]-methionine, using the plasmid pSPUTK expressing the various receptors as a template. The specific activity of labeled receptors will be determined by SDS-PAGE separation and autoradiography. Anti-FKBP52 Hi52C (10 µg) or negative control antibody (10 µg, antibody directed against a protein not present in the reticulate lysate) will be bound to Protein-A Sepharose (Amersham-Pharmacia Biotech, Piscataway, N.J.) for about 30 min. at room temperature in binding buffer (20 mM Tris, pH 8.0, 50 nM NaCl). Immune resins will be washed (3×1 ml) with wash buffer (20 mM Tris, pH 7.4, 50 nM NaCl, and 0.5% Tween 20) and added to 100 µl rabbit reticulocyte lysate (Green Hectares, Oregon, Wis.), supplemented with radiolabeled receptors and an ATP regenerating system (10 mM phosphocreatine plus 50 µg/ml creatine phosphokinase). The reactions will be incubated at 30° C. for about 30 min. without addition, or in the presence of hormone (100 nM), the Hsp90-inhibitor geldanamycin (36 mM; LC Laboratories, Woburn, Mass.), or the peptidylprolyl isomerase inhibitor FK506 (2 mM; LC Laboratories, Woburn, Mass.), all of which should disrupt receptor-Hsp90-FKBP complex formation. Resin complexes will then be washed (3×1 ml) with ice-cold wash buffer, and bound proteins will be extracted into SDS sample buffer and separated by SDS-PAGE. The gels will then be stained with Coomassie blue to visualize total proteins, and then dried and autoradiographed to visualize the radiolabeled receptors. To control for a loss of Hsp90 binding, as opposed to receptor binding, the co-immunoprecipitations will also be performed using an anti-Hsp90 antibody (H90-10, gift of David Toft, Mayo Clinic, Rochester, Minn.).

Example 5

Whole Cell Hormone Binding Assays

In an embodiment, HeLa cells exogenously expressing wild type AR or AR mutants, in addition to the various FKBP52 proteins, were grown to about 75% confluence in 6-well plates. The concentrations for tritiated hormones in these assays to produce a full saturation curve ranged between about 1 and 100 nM. In one embodiment, duplicate wells were treated with the same concentration of [$^3$H]-DHT plus a 1000-fold molar excess of unlabeled DHT, although other AR binding hormones could be used. After about 4 hrs. at 37° C., the wells were washed 4 times with phosphate buffered saline (PBS) warmed to 37° C. The cells were then lysed by adding 100 µl of M-PER reagent (Pierce, Rockford, Ill.) and rocking the plates at room temperature for 15 minutes.

An aliquot (20-50 µl) of each sample well was used for liquid scintillation counting, and the total cellular protein concentration was determined (Coomassie Plus, Pierce, Rockford, Ill.) for each well. The data were normalized for cell number variation by dividing the counts by the protein concentration for each well (dpm/µg of protein). Any hormone binding observed in those wells treated with a 1000-fold molar excess of unlabeled hormone was taken to represent non-specific binding and was subtracted from the specific binding data.

Example 6

PSA Protein Expression

The amount of PSA protein expression levels was measured in cells from the prostate cancer cell line LNCaP, after treatment with either control, or about 1 to 100 µM of each of the four FTA compounds identified in the screen (Compounds 1-4). The protein was quantified by an immunohistochemical method using photodetection.

LNCaP cells were maintained in RPMI-1640 medium containing 10% fetal bovine serum. Forty eight hours prior to the experiment, cells were washed several times in serum-free medium and then cultured in RPMI-1640 medium containing 10% charcoal-stripped fetal bovine serum (to remove endogenous androgens). After 48 hours in this medium, Compound 2 was added in a range of concentrations (0, 3, 10, 30, and 100 µM) for 24 hours, at which time the synthetic androgen, methyltrienolone (R1881), (Sigma, St. Louis, Mo.) was added (0.5 nM). After an additional 48 hours, cells were lysed as described in Yano A., et al., Proc. Natl. Acad. Sci. USA, 105:15541-46 (2008), and PSA protein was monitored by polyacrylamide gel electrophoresis and Western blotting with an anti-PSA antibody (se-80304, Santa Cruz Biotechnology).

FIG. 6B shows the effect of Compound 2 on expression of PSA protein expression after exposure to the cells for about 48 hours. At 100 µM, mRNA expression was decreased to 20% of control levels. Thus, the data show that decreased mRNA and protein expression of PSA is due to the effect of the FTA compounds inhibiting the AR mediated effect, rather than a cellular decrease in protein expression due to some other non-specific effect of the FTA compounds.

Example 7

PSA mRNA Quantitation

For PSA mRNA determination, cells were cultured and treated identically, except that lysis for mRNA extraction was performed 24 hours after addition of R1881. Total RNA was isolated using protocols and reagents contained in the Qiagen RNeasy Kit (Valencia, Calif.). TaqMan real-time quantitative RT-PCR analysis of PSA was performed using previously described techniques Hong T A, et al., Cancer Res., 65:7763-74 (2005); Guo F, et al., Cancer Res., 65:10536-44 (2005). The amount of PSA mRNA level and total protein in cells from the prostate cancer cell line LNCaP was measured after treatment with either control, or about I to 100 µM of each of the four compounds identified in the screen (Compounds 1-4). It was known that the expression of PSA mRNA in LNCaP cells is driven by an androgen receptor mediated pathway. The mRNA is quantified by a photodetection method over time. FIG. 6A shows the effect of Compound 2 on expression of PSA mRNA after exposure to the cells for 24 hours. At 100 µM, mRNA expression was decreased to 40% of control levels.

Example 8

Measurement of AR Nuclear Translocation

LNCaP cells were maintained as above. At 50% confluence, cells were washed several times in serum-free RPMI- 1640 medium, and re-cultured for 48 hours in RPMI-1640 medium containing 10% charcoal-stripped fetal bovine serum. At that time, compound 2 (termed 21D1C in FIG. 7) was added to a final concentration of about 30 µM. After an additional 24 hours, R1881 was added (0.1 nM) and cells were cultured for an additional 2 hours. At that time, cells were lysed and separated into nuclear and cytosolic fractions following published methods (Schreiber, et al., Nucleic Acids Res., 17:6419 (1989)). Quantification of AR in nucleus and cytosol was performed by Western blotting with an AR-specific antibody following polyacrylamide gel electrophoresis. Appearance of AR in the nuclear fraction following treatment with R1881 represents ligand-dependent nuclear translocation of AR, which is significantly prevented by pre-treatment with compound 2 (FIG. 7).

Example 9

Scintillation Proximity Binding Assay

In order to determine whether the FTAs of the present invention were binding to the AR binding site for DHT, as a competitive inhibitor, a ligand competition assay was performed based on the methods of Féau, C., et al., J. Biomol. Screen. 14:43-48 (2009).

All liquid handling was carried out using an automated liquid handling system (Biomek FX). To each well of a 384-well Ni-chelate coated Flashplate® (PerkinElmer) was added 50 µl of 5 µM nuclear receptor ligand binding domain (NR-LBD) in assay buffer. After about a 30-60 minute incubation, the protein solution was discarded (followed eventually by washes with assay buffer). About 25 µl of serially diluted FTAs in assay buffer containing 10% DMSO were added into each well followed by addition of 25 µl of a radioligand solution in assay buffer. The final assay solution contained 5% DMSO. The plates were sealed with clear tape (Millipore® tape multiscreen) and allowed to equilibrate for 5 hours at room temperature, or 4° C. For the AR binding assay, [3H]-DHT was used at a final concentration of 20 nM and the assay buffer contained 50 mM HEPES, 150 mM $Li_2SO_4$, 0.2 mM TCEP, 10% glycerol, 0.01% Triton X-100, pH 7.2. Radiocounts were measured using a TopCount Microplate Scintillation and Luminescence Counter (Packard Instrument Company). All data were analyzed using GraphPad Prism 4.03 (GraphPad Software, San Diego, Calif.); IC50 values were obtained by fitting data to equation (Sigmoidal dose-response (variable slope)): y=Bottom+(Top-Bottom)/(1+10^((Log IC50−x)*Hillslope)); x is the logarithm of concentration; y is the response. Two independent experiments, in triplicates, were carried out for each compound.

The resulting sigmoid curve (FIG. 8) shows the dose dependant binding of labeled DHT to the AR binding site. The flat curves to the right are the different concentrations of FTAs, meaning that none of the FTA compounds tested competitively inhibited DHT binding.

Example 10

Fluorescence Polarization Binding Assay

A fluorescence assay was performed to determine whether the FTAs of the present invention bind to the same site as SRC peptide, which mimics the binding of FKBP52, using the method of Estebanez-Perpina, E., et al., (2007), infra.

Plates (384 wells; Costar 3710) were prepared with 4 µl of compound (5 mM in DMSO) plus 80 µl of dilution buffer (20 mM Tris HCl 100 mM NaCl, pH 7.2/1 mM DTT/1 mM EDTA/0.01% Nonidet P-40/10% glycerol/10.5% DMSO) by using a WellMate (Matrix). Five microliters from the dilution plates was transferred to 384-well assay plates followed by 20 µl of protein mixture (6.25 µM AR plus DHT and 0.0125 µM peptide in dilution buffer; final concentration 50 µM compound, and 4% DMSO). Fluorescence polarization (FP) was measured after about 2 h (excitation 485 nm, emission 530 nm) on an AD plate reader (Molecular Devices). For measuring dose-response, compounds were diluted from 0.005 to 500 µM in DMSO into a 96-well plate (Costar 3365). About twenty microliters of mixture was added to 1.2 µl of compounds in 384-well plates (Costar 3710), yielding a final concentration of 5 nM to 500 µM, and equilibrated for 5 h before FP. Data were analyzed by using SigmaPlot 8.0 (SPSS, Chicago, Ill.), and Kd values were obtained by fitting data to y minimum (maximum minimum)/1 (x/Kd) Hill slope.

When SRC2-3 was tested, the FTA did not show any competition for the FKBP52 binding site (curves are flat). In FIG. 9B, total fluorescence intensity is measured simultaneously as FP, to insure that no interference coming from the test compound itself is occurring in the assay. The Figure shows there is no change in total fluorescence detected for each FTA, and there is no fluorescence interference, which confirms that mP values of FIG. 9A are valid.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of identifying a compound in vitro which inhibits FKBP52-enhanced, androgen receptor (AR)-mediated activity, the method comprising:
   a) providing an AR tester cell, the tester cell comprising a murine embryonic fibroblast derived from FKBP-52 deficient mice, the tester cell being transfected with a DNA encoding AR, an AR-responsive reporter plasmid, and a vector encoding a FKBP52 protein;
   b) providing a control cell, the control cell comprising the murine embryonic fibroblast derived from FKBP-52 deficient mice, the control cell being transfected with the DNA encoding AR, the AR-responsive reporter plasmid, and a vector that does not encode FKBP-52;
   c) contacting the cell of a) and b) with a test compound;
   d) contacting the cell of a) and b) with an AR agonist;
   e) incubating the cell of a) and b) for a period of time;
   f) measuring an amount of AR-responsive reporter expression in a) and b); and
   g) comparing the amount of AR-responsive reporter expression in the cell of a) and b),
   wherein the test compound is identified as inhibiting FKBP-52-enhanced, AR-mediated activity when the amount of AR-responsive reporter expression in the cell of a) is less than the amount of AR-responsive reporter expression in the cell of b).

* * * * *